United States Patent [19]

Schär et al.

[11] Patent Number: 4,826,313
[45] Date of Patent: May 2, 1989

[54] METHOD OF ANALYSIS

[75] Inventors: Rudolf W. Schär, Aesch; Rita Hofmann-Sievert, Marly, both of Switzerland

[73] Assignee: Ciba-Geigy Corporation, Ardsley, N.Y.

[21] Appl. No.: 201,262

[22] Filed: May 31, 1988

Related U.S. Application Data

[63] Continuation of Ser. No. 908,770, Sep. 18, 1986, abandoned.

[30] Foreign Application Priority Data

Sep. 26, 1985 [CH] Switzerland .................. 4185/85

[51] Int. Cl.[4] ............... G01N 21/33; G01N 21/35; G01N 21/59
[52] U.S. Cl. ........................... 356/51; 250/343; 250/373; 356/300
[58] Field of Search ............... 356/51, 300; 250/343, 250/373

[56] References Cited

U.S. PATENT DOCUMENTS

| 3,433,570 | 3/1969 | Hansen | 356/128 |
| 3,751,672 | 8/1973 | Michel et al. | 356/133 |
| 4,602,869 | 7/1986 | Harrick | 356/246 |

FOREIGN PATENT DOCUMENTS 75353 3/1983 European Pat. Off. .

OTHER PUBLICATIONS

Hansen, *Analytical Chemistry*, vol. 35, No. 6, May, 1963, pp. 765 and 766.
Katlafsky et al., *Analytical Chemistry*, vol. 35, No. 11, Oct., 1963, pp. 1665–1670.
Hansen, *Analytical Chemistry*, vol. 36, No. 4, Apr., 1964, pp. 783–787.
Wilks, "Internal Reflection Spectroscopy", in *Internat. Lab.*, Jul./Aug., 1980, pp. 47–55.
Harrick, "Prism Liquid Cell", in Applied Spectroscopy, 37, 573–575 (1983).

*Primary Examiner*—F. L. Evans
*Attorney, Agent, or Firm*—Wenderoth, Lind & Ponack

[57] ABSTRACT

The invention relates to a method of analyzing solutions and dispersions of dyes or their precursors and intermediates by optical and/or spectroscopic measurements, which method comprises using apparatus based on the principle of attenuated total reflection as sensor system. The advantage of the invention is that even highly concentrated, strongly colored solutions can be analyzed without prior dilution, as can also dye dispersions without separation of the solids content.

11 Claims, 1 Drawing Sheet

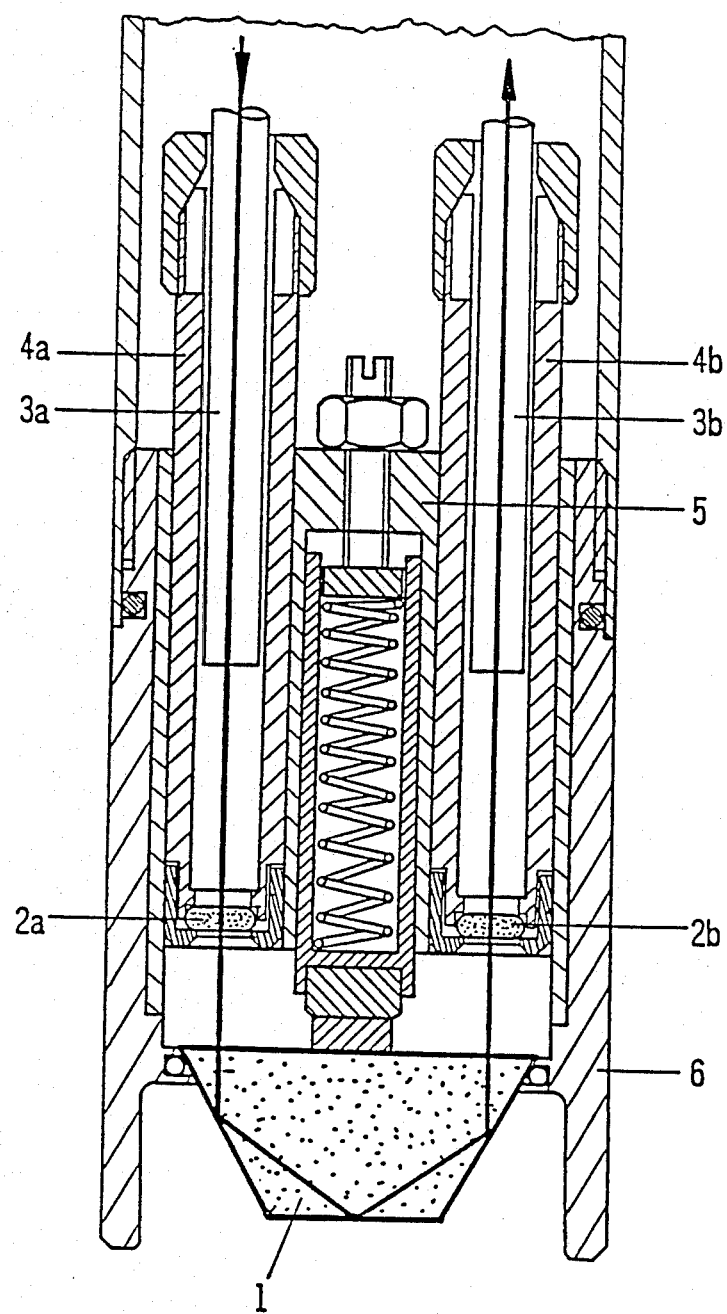

METHOD OF ANALYSIS

This application is a continuation of application Ser. No. 908,770, filed Sept. 18, 1986, now abandoned.

BACKGROUND OF THE INVENTION

The present invention relates to a method of analysing solutions or dispersions of dyes or their precursors and intermediates by an optical and/or spectroscopic technique, which method comprises using apparatus based on the principle of attenuated total reflection as sensor system.

In recent years, increasing efforts have been made to automate dye manufacture, both with respect to the actual preparatory process itself and to the working up. To obtain satisfactory and reproducible results it is necessary to rely on analytical methods which are characterised by the following criteria: short duration of analysis, high frequency of analysis, low costs, simplicity, reliability and space requirement. Apparatus that meets these requirements consists in particular of sensors for pressure, temperature and pH measurement. Also important, especially in the dyestuffs sector, is the recording of optical data preferably in a wide wavelength range. Spectroscopic methods have attained importance with the development of fibre optical waveguides, as measuring apparatus and measuring cell can now be installed separately. The advantages of spectroscopic methods reside in their high selectivity, thereby also making possible the rapid analysis of complex organic mixtures without complicated separation procedures. Further, this method of analysis ideally meets the requirements mentioned at the outset.

Important for making optical measurements in the visible or also infrared, and ultraviolet range is suitable apparatus for passing the beam of light used for the analysis through the liquid medium. The simplest piece of equipment is a flow cell which, however, usually requires a by-pass through which the medium to be analysed is continually circulated. In addition, particles on which the light is scattered prove exceedingly troublesome in this method. Aside from the flow cell, other systems which are solely immersed in the medium to be analysed have meanwhile been developed. These systems have become generally known as optical sensors (Optrodes ®). Optical sensors for measuring transmission consist e.g. of a two-way bundle of fibres and a mirror. However, for measuring stray light and reflectivity, similar constructions without mirror are employed. The most serious drawback of such optical sensors and of the flow cell is, however, that concentrated solutions or solutions with a solids content cannot, or can no longer, be analysed accurately and reproducibly. But the fact is that strongly absorbing and highly concentrated solutions are the rule in dyestuff chemistry. Analysis of such solutions is therefore always preceded by a complicated sampling involving repeated dilution and/or separation of undissolved components. This sampling is time-consuming and errors are inherent in it. Continuous monitoring of a process in this manner is virtually impossible.

SUMMARY OF THE INVENTION

Hence it is the object of the present invention to provide an optical system which can be employed even for the analysis of concentrated, highly coloured solutions and dispersions, and to develop a method of analysing such media that does not require dilution and which can be carried out continuously on-line. It has been found that sensors based on the principle of attenuated total reflection are preeminently suited to this purpose.

Accordingly, the present invention relates to a method of analysing solutions and dispersions of dyes or their precursors and intermediates by means of optical and/or spectroscopic measurements, which method comprises using apparatus based on the principle of attenuated total reflection as sensor system.

BRIEF DESCRIPTION OF THE DRAWING

The drawing is a schematic of a sensor employed for carrying out a method of analyzing solutions and dispersions of dyes or their precursors and intermediates by an attenuated total reflection technique in accordance with the present invention.

DETAILED DESCRIPTION OF THE INVENTION

If a beam of light strikes the boundary surface between a medium of high optical density and a medium of lower optical density, the light will be totally reflected if the angle of incidence is greater than the critical angle. In total reflection, however, the beam of light travels a certain distance in the medium of lower optical density. The depth of penetration and the effective layer thickness are functions of the refractive indices, of the angle of incidence, of the wavelength and of the polarisation: they lie approximately in the order of magnitude of the wavelength of light. In the course of its pathway in the medium of low optical density, the light interacts therewith. In doing so it may become attenuated by absorption, hence the term "attenuated total reflection" (abbreviated to ATR). As the effective layer thickness for the light entering the medium to be analysed has only about one wavelength, measurement is made virtually with an ultra-thin absorption cell. It is thus possible to analyse even highly concentrated solutions accurately without having to dilute them. As the exiting lightwave is a stationary wave that is not scattered on particles, it is also possible to measure inhomogeneous phases such as dye slurries or dispersions. The method itself is known and attention is drawn in this connection to the article by P. A. Wilks in International Laboratory, July/August 1980, pp. 47–55, and to N. J. Harrick, Internal Reflection Spectroscopy, published by N. J. Harrick, Ossining N.Y., USA, 1967 and 1979; F. M. Mirabella, N. J. Harrick, Internal Reflection Spectroscopy, Review and Supplement, published by N. J. Harrick, Ossining, N.Y., USA, 1985.

The core of the sensor for determining the attenuated total reflection at a specific or variable wavelength is a prism of light-permeable material with a refractive index higher than that of the dye solution to be analysed. Suitable materials, in addition to highly refractive glass such as heavy flint glass, are alumina (sapphire), diamond, strontium titanate, titanium oxide, zirconium oxide or quartz glass. Particularly good results are obtained with a sapphire crystal, as this material is fairly durable, is permeable in a wide wavelength range, and is also inexpensive. Prisms of different geometries are obtained, depending on whether it is desired to obtain a single or multiple refraction of the measuring beam. Quite generally, the sensitivity of the method increases with the number of reflections and also the depth of penetration of the measuring beam in the solution to be analysed, which depth depends directly on the refractive index. In the method of this invention, a sapphire prism, in particular a conical sapphire prism, has proved very suitable. The number of reflections of the beam of light in this prism is one, two or three.

Preferred embodiments of the method of this invention are characterised in that optical sensors can be used with single or multiple reflections, preferably with up to ten reflections, of the beam of light used for the analysis. A further area of the possible utilities, especially in the UV/VIS spectral range, is thereby covered. For example, sensors with single reflection are preferred for analysing strongly absorbing concentrated solutions. Optical sensors with multiple reflection, e.g. with 10 to 30 reflections, are better suited for analyses in less concentrated solutions and/or for analyses in the infrared range.

A particularly preferred embodiment of the method of this invention comprises using an optical sensor with one, two or three reflections of the beam of light.

There are a number of possibilities for directing the beam of light, in which connection the arrangement of the actual measuring instrument, e.g. the IR or UV/VIS spectrophotometer, is of importance.

A particularly advantageous arrangement is to have the spectrophotometer separate from the probe. This method saves space, the sensor can also be mounted only at sites that are difficult of access and, in addition, several sensors can be connected to one measuring instrument, i.e. one instrument suffices to process the information from several sensors.

To mount the sensor head not only in classical stirred reactors but also e.g. in the tube reactors frequently employed at the present time for the continuous synthesis of azo dyes, it was necessary to design the head as small as possible. It is advantageous in this connection to connect the base of the prism, especially of the sapphire crystal, with two approximately parallel fibre optical waveguides to form a rod-shaped probe which can also be readily mounted in tube reactors of small diameter. The beam of light used for the analysis is conducted by one of the waveguides and the totally reflected beam is deflected by the other.

It is also advantageous to combine the sensor and the appropriate measuring instrument with each other by means of fibre optical waveguides, so making possible a signal transmission over wide areas, e.g. up to 1000 m, which transmission is not hindered by electric or magnetic fields. A further advantage of the waveguides is that no special measures need be taken regarding explosion prevention. In principle, the possibility also exists of using in this invention sensors that already contain light source and/or detector in the sensor head.

A preferred embodiment of the method of this invention comprises measuring spectral data from the infrared to the ultraviolet range. It is especially preferred to measure UV and UV/VIS spectral data.

The illustration shows a sensor employed for carrying out the method as described herein. The lower part houses the conical sapphire 1, which is retained in the casing by means of an overhead spring. Right and left of the spring are the two parallel fibre optical waveguides 3a and 3b in clamps 4a and 4b. The waveguides end in front of optical lens systems 2a and 2b, which bundle the light beam between waveguide and prism. The reference number 5 shows the inside of the casing with the clamp for the spring and 6 indicates the outer casing of the sensor. The sensor has a sufficiently high density, even in aggressive media, and is conveniently mounted such that it is immersed direct in the solution to be analysed.

Depending on the light-permeability of the prism, it is possible to cover a wide wavelength range with this method and a measurement made in this range, depending on the problem, at a fixed or variable wavelength. For the analysis of dye solutions, the wavelength range from infrared to ultraviolet is especially important. Depending on the maximum absorption of the dye, one or more specific wavelengths or one narrow wavelength will be selected.

The dyes whose synthesis and processing will be controlled and monitored by the method described herein are primarily textile dyes belonging to a very wide range of chemical classes. They are for example anionic dyes such as nitro, aminoketone, ketoneimine, methine, nitrodiphenylamine, quinoline, aminonaphthoquinone or coumarin dyes, or also dyes based on fustic extract, in particular acid anthraquinone and azo dyes such as monoazo and disazo dyes. Further suitable dyes are basic, i.e. cationic, dyes. These are for example the halides, sulfates, methosulfates or metal halide salts, e.g. tetrachlorozincates of azo dyes such as monoazo, disazo and polyazo dyes, of anthraquinone dyes, phthalocyanine dyes, diphenylmethane and triarylmethane dyes, methine, polymethine and azomethine dyes, of thiazole, ketoneimine, acridine, cyanine, nitro, quinoline, benzimidazole, xanthene, azine, oxazine and thiazine dyes.

In the present context, the term "dyes" shall also be understood as comprising fluorescent whitening agents, e.g. of the stilbene type, especially those of the bis-triazinylaminostilbenedisulfonic acid, bisstyrylbiphenyl and bisstyrylbenzene and bistriazolylstilbenedisulfonic acid types.

It will be readily understood that, depending on the problem to be solved in the course of the dye synthesis, the method of this invention is also applicable to precursors and intermediates in addition to the actual dyes and fluorescent whitening agents. The by-products formed during the reaction are of particular importance not only as regards yield, but also as regards the shade or inherent colour of the dye or flourescent whitening agent in question.

By appropriate choice of materials for the prism and the fibre optical waveguides, the method of this invention is e.g. most suitable for determining the diazonium ion concentration, which is readily possible by measuring the intensity of the $N\equiv N$ stretching frequency by infrared spectroscopy in a wavelength range from 4 to 5 nm. For this utility, the sensor is connected to an IR spectrophotometer as measuring instrument. By irradiation with light having a wavelength at which the $N\equiv N$ stretching frequency is activated, it is possible to monitor the change in the diazonium ion concentration as a function of the time, in this case the reaction time.

In principle, the method of this invention is susceptible of broad application and can be used in dye manufacture for controlling and monitoring dye synthesis and educt and product streams, for analysis and for quality control. The method is particularly suitable for determining the concentration of dye solutions, i.e. of true solutions as well as of solutions that contain solids, for example finely dispersed dye;

monitoring the crystallisation/salting out of dyes, whereby the amount of salt can be readily controlled and an excess of salt that would result in wastewater pollution avoided;

analysing the product/educt ratio and detecting by-products in the dye synthesis, thereby making it readily possible to determine the time at which the reaction mixture contains a maximum of product and a minimum of by-products;

monitoring product/educt streams in syntheses which are carried out continuously.

The invention is illustrated by the following Examples.

Example 1
Synthesis of dinitrostilbenedisulfonic acid (DNS)

Dinitrostilbenedisulfonic acid is prepared from p-nitrotoluenesulfonic acid by oxidation with sodium hypochlorite (NaOCl). Colourless and coloured intermediates and by-products are formed during the synthesis. Their concentration depends on the reaction conditions and the reaction time, because the product is not stable under the reaction conditions. It is therefore necessary to find the optimum time at which as much educt and intermediate as possible is consumed and as little product as possible is destroyed.

The educt and the colourless intermediates and by-products, which are of little relevance as regards quality, have similar spectra in the UV/VIS range with a maximum absorption at c. 280 nm. In marked contrast, DNS has a maximum absorption at c. 360 nm and the coloured by-products absorb still further in the visible range with a broad maximum at c. 460 nm. Normally no absorption occurs at above 700 nm, so that 750 nm may serve as reference wavelength. The analysis is carried out with the sensor shown in the illustration according to the method of attenuated total reflection.

By measuring the spectral data during the reaction and evaluating them, the following information is obtained and can be used for process control:

best time for terminating the reaction (derivation of the DNS absorption with respect to time becomes zero);

yield control (by measuring the final absorption value);

control of the reaction conditions, with deviations being expressed by a greater increase in coloured by-products;

quality control by determining the concentration of coloured by-products;

control of rate of addition of the starting component (NaOH) by measuring the starting kinetics (thereby achieving an improvement in reproducibility).

The optical sensor, inserted into a by-pass, and the photometer, housed in the control room, are about 25 m apart.

Additional measurements are made for further process development (e.g. determining the optimum reaction temperature), thereby making it possible to find improved reaction conditions rapidly with a minimum of separation analysis.

Example 2
Adjusting the concentration of a solution of diaminostilbenedisulfonic acid Diaminostilbenedisulfonic acid is obtained as an aqueous suspension in a concentration of c. 18% after a production step and is adjusted for the subsequent operation to a 14% solution in an accuracy of ±0.1% (absolute). This is achieved very accurately by measuring the wavelength of the maximum absorption (350 nm) and by comparison with a linear calibration curve, omitting volume measurement and metering devices. The analysis is carried out with the sensor shown in the illustration using the method of attenuated total reflection.

Here there is a very wide range of application for adjusting concentration/strength in the course of production processes or for liquid commercial forms.

Example 3
Filtrate value and control of salt consumption in crystallisation or precipitation (salting out of diaminostilbenedisulfonic acid)

The decrease in concentration of the dissolved amount of diaminostilbenedisulfonic acid is monitored immediately upon addition of salt (preferably NaCl). The solids content causes no trouble up to the end point. The amount of salt required for salting out (c. 20%) can be optimised and the filtrate value (absorbance $\leq 0.025$) controlled by these measurements. The crystallisation form can be controlled by observing the onset of precipitation (at c. 5-10% of NaCl, depending on the temperature).

The method is generally applicable, e.g. for salting out water-soluble dyes and fluorescent whitening agents and for crystallisations from hot solutions.

Example 4
Sulfonation of a zinc phthalocyanine

The degree of sulfonation in 40% oleum at c. 95° C. is determined by the reaction time. To find the end point, it is usual to investigate a sample spectrophotometrically after exactly 2 hours. The end point of the reaction is extrapolated from the ratio of the absorption bands in the visible range (666 and 628 nm). Measured with the optical sensor it is not possible to use the bands in the visible range because they are insufficiently resolved in the undiluted sample. The ratio of two absorption bands in the UV range (230 and 320 nm) likewise changes increasingly and steadily in the course of the reaction. The optimum end point of the reaction is reached when this ratio is exactly 1.

What is claimed is:

1. A method of analyzing solutions and dispersions of dyes or their precursors and intermediates by optical or spectroscopic measurements, which method comprises immersing an optical sensor working on the principle of attenuated total reflection into said solutions or dispersions, reading an output of the sensor, and monitoring product/educt streams in syntheses which are carried out continuously.

2. A method for analyzing a solution or dispersion of a dye or its precursors and intermediates by optical or spectroscopic measurements, which method comprises immersing an optical sensor into said dispersion or solution, reading an output of the sensor, and monitoring product/educt streams in systheses which are carried out continuously, the sensor comprising:
   (a) a prism of light-permeable material with a refractive index greater than that of the solution or dispersion, said prism being connected to a casing for the sensor but contacting the solution or dispersion;
   (b) two fiber optical waveguides embedded in said casing, one incident-beam waveguide to guide the incident beam to the prism, and the second reflected-beam waveguide to guide the reflected beam from the prism; and (c) two optical lens elements, one oriented to bundle the incident beam between the incident-beam waveguide and the prism, and the second oriented to bundle the reflected beam between the reflected-beam waveguide and the prism.

3. A method according to claim 2 wherein said prism effects one to ten reflections of the incident beam.

4. A method according to claim 3 wherein said prism effects one, two or three reflections.

5. A method according to claim 4 wherein said prism effects one reflection.

6. A method according to claim 2 wherein said prism is made of alumina, diamond, strontium titanate, titanium oxide, zirconium oxide or quartz glass.

7. A method according to claim 6 wherein said prism is made of alumina in the form of sapphire crystal.

8. A method according to claim 2 wherein said two fiber optical waveguides are positioned in a parallel orientation.

9. A method according to claim 2 wherein the sensor is connected to a measuring instrument by fiber optical waveguides.

10. A method according to claim 2 wherein the sensor is sensitive to electromagnetic energy in the ultraviolet, visible or infrared range.

11. A method according to claim 10 wherein the sensor is sensitive to energy in the ultraviolet and visible range.

* * * * *